US010391044B2

(12) United States Patent
Vemishetti et al.

(10) Patent No.: US 10,391,044 B2
(45) Date of Patent: Aug. 27, 2019

(54) LOW WATER DENTIFRICE COMPOSITIONS

(71) Applicant: Colgate-Palmolive Company, New York, NY (US)

(72) Inventors: Kavita Vemishetti, Brooklyn, NY (US); Linh Fruge, Hillsborough, NJ (US); Michael Prencipe, West Windsor, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/570,430

(22) PCT Filed: May 1, 2015

(86) PCT No.: PCT/US2015/028854
§ 371 (c)(1),
(2) Date: Oct. 30, 2017

(87) PCT Pub. No.: WO2016/178652
PCT Pub. Date: Nov. 10, 2016

(65) Prior Publication Data
US 2018/0147125 A1   May 31, 2018

(51) Int. Cl.
*A61K 8/24* (2006.01)
*A61K 8/27* (2006.01)
*A61K 8/36* (2006.01)
*A61Q 11/00* (2006.01)
*A61K 8/21* (2006.01)
*A61K 8/19* (2006.01)

(52) U.S. Cl.
CPC .................. *A61K 8/24* (2013.01); *A61K 8/19* (2013.01); *A61K 8/21* (2013.01); *A61K 8/27* (2013.01); *A61K 8/36* (2013.01); *A61Q 11/00* (2013.01); *A61K 2800/28* (2013.01); *A61K 2800/30* (2013.01); *A61K 2800/31* (2013.01); *A61K 2800/5922* (2013.01)

(58) Field of Classification Search
None
See application file for complete search history.

(56) References Cited

U.S. PATENT DOCUMENTS

| 2,946,725 | A | 7/1960 | Norris et al. |
| 3,070,510 | A | 12/1962 | Cooley et al. |
| 3,538,230 | A | 11/1970 | Pader et al. |
| 3,678,154 | A | 7/1972 | Widder et al. |
| 3,862,307 | A | 1/1975 | Di Giulio |
| 3,989,814 | A | 11/1976 | Cordon et al. |
| 4,022,880 | A | 5/1977 | Vinson et al. |
| 4,235,874 | A | 11/1980 | Norfleet |
| 4,340,583 | A | 7/1982 | Wason |
| 4,647,451 | A | 3/1987 | Piechota, Jr. |
| 5,004,597 | A | 4/1991 | Majeti et al. |
| 5,578,293 | A | 11/1996 | Prencipe et al. |
| 5,589,160 | A | 12/1996 | Rice |
| 5,603,920 | A | 2/1997 | Rice |
| 5,624,906 | A * | 4/1997 | Vermeer .................. A61K 8/60 514/23 |
| 5,651,958 | A | 7/1997 | Rice |
| 5,658,553 | A | 8/1997 | Rice |
| 5,670,137 | A | 9/1997 | Ascione |
| 5,716,601 | A | 2/1998 | Rice |
| 6,190,644 | B1 | 2/2001 | McClanahan et al. |
| 6,685,920 | B2 | 2/2004 | Baig et al. |
| 6,696,045 | B2 | 2/2004 | Yue et al. |
| 8,481,004 | B2 | 7/2013 | Brown et al. |
| 8,865,137 | B2 | 10/2014 | Morgan et al. |
| 2004/0146466 | A1* | 7/2004 | Baig ........................ A23G 4/06 424/49 |
| 2012/0207686 | A1 | 8/2012 | Fruge et al. |
| 2012/0282192 | A1 | 11/2012 | Miller et al. |
| 2018/0243588 | A1 | 8/2018 | Fisher et al. |
| 2018/0243589 | A1 | 8/2018 | Fisher et al. |

FOREIGN PATENT DOCUMENTS

| EP | 0 638 307 | 2/1995 |
| WO | 1998022079 | 5/1998 |
| WO | 2014088573 | 6/2014 |
| WO | 2014099164 | 6/2014 |
| WO | 2014204959 | 12/2014 |
| WO | 2015028096 | 3/2015 |

OTHER PUBLICATIONS

International Search Report and Written Opinion of the International Searching Authority in International Application No. PCT/US2015/028854, dated Nov. 13, 2015.
Harry et al., 2000, "Harry's Cosmeticology, Oral Care Products," Cosmeticology, Chemical Publishing Co., Inc. pp. 725-755.

* cited by examiner

*Primary Examiner* — Nannette Holloman

(57) ABSTRACT

The present disclosure provides low water dentifrice compositions comprising an effective amount of a zinc ion source, a stannous ion source, a polyphosphate and an acid in a calcium pyrophosphate base. The acid lowers the pH of the composition to enable stabilization of the metal ions and extend shelf-life of the composition.

15 Claims, No Drawings

LOW WATER DENTIFRICE COMPOSITIONS

FIELD OF THE INVENTION

The present disclosure relates to low water dentifrice compositions comprising an effective amount of a zinc ion source, a stannous ion source, polyphosphates and acid in a calcium pyrophosphate base. The acid lowers the pH of the composition to enable stabilization of the metal ions and extend the shelf-life of the composition.

BACKGROUND

Calcium pyrophosphate has been used as an abrasive in dentifrice compositions in the past, but it has rarely been used as the primary abrasive agent because of its extremely high abrasiveness (the radioactive dentin abrasion, RDA, of calcium pyrophosphate can be over 1000 as a 50% aqueous slurry). Instead, calcium pyrophosphate has been usually been added as a secondary polishing agent in compositions based on a primary silica abrasive to increase the abrasiveness of the composition. In addition, like other calcium salts, calcium pyrophosphate suffers from the drawback that in solution it will react with soluble fluoride sources resulting in the precipitation of calcium fluoride. This negatively impacts the composition by removing the fluoride ions that provide important oral care benefits.

Polyphosphates and ionic active ingredients have been used in dentifrices to promote oral health. Polyphosphates are known anti-tartar agents that help retard calculus formation. Metal ions such as stannous and zinc ions are known to be effective anti-microbial agents. These metal ions provide anti-gingivitis and anti-plaque benefits and may also improve breath and reduce tooth or gum sensitivity. Stannous fluoride has been used in dentistry since the 1950's as a fluoride source to prevent dental caries. Similarly, zinc citrate has been shown to have anti-plaque, anti-gingivitis and anti-tartar efficacy. In addition, zinc has also shown efficacy as an anti-malodor agent.

While such actives have previously been used in dentifrices, for several reasons, it has proven challenging to provide these actives together in a stable single phase composition. One such technical problem is to preserve the bioavailability of stannous ions and maximize the chemical stability of the stannous ion source. Many formulations suffer from the problem that the bioavailable levels of stannous and/or zinc drop during aging (e.g., shelf storage). This drop can result in a bioavailable level of stannous and/or zinc as much as 50% less than the formulation quantity. In addition, certain polyphosphates are unstable in high-water aqueous systems. Such polyphosphates in an aqueous system are susceptible to hydrolysis unless they are present at a high pH, which is not compatible with high stannous availability. Stannous fluoride tends to precipitate stannous ions in aqueous environments, thereby reducing the efficacy and availability of the stannous ions in the oral care composition. Additionally, polyphosphates can react with ionic fluoride in oral compositions at ambient temperature to produce monofluorophosphate ions, altering the pH of the composition. This reaction compromises the efficacy of the oral composition and its ability to provide stable ionic fluoride and polyphosphate to the oral surfaces.

Other attempts to provide such efficacious dentifrice compositions have reduced the amount of water present in the composition. Reducing the amount of water would theoretically reduce or eliminate the stability issues associated with the fluoride, polyphosphate and other ionic actives. However, reducing the level of water, and optionally replacing some or all of the removed water with a humectant, creates problems in obtaining acceptable rheology and thickening properties in the composition. When water, which is a highly polar solvent, is removed, conventional thickening agents such as carboxymethylcellulose ("CMC") tend to inadequately gel up. Attempts to reduce water content in dentifrice compositions have included the dentifrices described in, e.g., EP 0 638 307 B1; U.S. Pat. Nos. 4,647,451; and 5,670,137. Such known formulations have been shown to exhibit progressive thickening over time, which prolongs the time period to reach a rheological steady state, or even prevents the dentifrice from reaching a rheological steady state. Ideally, dentifrice formulations need to reach a steady state for consumer acceptance within two weeks. If a formulation routinely increases in viscosity over time, dispensing of the formulation will become difficult, which will likely result in consumer dissatisfaction.

U.S. Pat. No. 6,696,045 discloses dentifrice compositions comprising a single low water phase comprising polyphosphate and ionic active ingredients. Although compositions comprising glass H polyphosphate, which has a long chain of about 21 phosphate groups, and sodium or stannous fluoride are disclosed, with the sodium fluoride being optionally combined with zinc citrate and the stannous fluoride being optionally combined with zinc lactate, there is no disclosure of how to combine stannous, fluoride and zinc salts in a low water composition in combination with short chain length polyphosphates in a low water single phase system.

Other attempts to provide dentifrice compositions having these actives in efficacious amounts involved the use of dual compartmented packaging wherein the reactive ingredients are physically separated until the time of brushing. (See, e.g., WO98/22079, "Dentifrice Compositions Containing Polyphosphate and Fluoride.") However, such dual-compartmented packages are typically considerably more expensive than the conventional laminate tubes that have been used for many years to contain and dispense dentifrices. They also may be problematic in terms of ease of consumer use and uniform dispensing of approximately equal amounts of each composition during each consumer use. Another approach that has been used is the encapsulation of the metal ion sources in a polymer matrix, but this adds considerably complexity to the formulation of the composition.

BRIEF SUMMARY

There is a need in the art to provide dentifrice compositions that can effectively combine sources of stannous, fluoride, and zinc ions in combination with a polyphosphate in a low water or zero water single phase system that has efficacious delivery of water-unstable actives and/or actives that are reactive with respect to each other in a single phase. There is also a need in the art to provide low water single phase dentifrice compositions that have an improved rheological profile, and in particular, have a stable rheology that effectively reduces or eliminates progressive thickening of the composition over time which in turn provides a composition that can effectively be dispensed over the period of its shelf life.

The inventors have developed a low-water dentifrice composition based on calcium pyrophosphate abrasive that achieves these objectives. In the present disclosure, the embodiments described herein provide a dentifrice composition comprising: an orally acceptable vehicle; calcium pyrophosphate; a source of fluoride ions; a source of stannous ions; a source of zinc ions; and at least one polyphosphate salt; at least one acid; and wherein the dentifrice composition is a low-water composition, preferably a zero-water composition (e.g., no added water). Preferably, the composition is a single phase composition.

As will be demonstrated herein, the preferred embodiments can provide a dentifrice that provides multiple therapeutic benefits by combining stannous ions and fluoride ions, e.g., as stannous fluoride, zinc ions, e.g. as zinc citrate, and polyphosphates, e.g., in the form of tetrasodium pyrophosphate/sodium tripolyphosphate, in a base composition comprising calcium pyrophosphate. The use of particular acids, optionally as part of a buffer system, can stabilize the stannous ions in the presence of the zinc ions and polyphosphates, and leave the stannous ions active in the low water composition for effective anti-microbial action when used for cleaning the teeth.

The preferred embodiments of the present disclosure provide compositions that have a total water content of less than about 1% by weight, for example, 0% water (no added water).

The preferred embodiments of the present disclosure also may provide a low water or zero water dentifrice system that retains greater than 50% of bioavailable metal ions during storage, for example, greater than 60% or greater than 70%.

The preferred embodiments of the present disclosure also may provide a low water or zero water dentifrice system having a stable rheology that does not tend to progressively thicken over time, but instead thickens quickly, for example within a few days of manufacture, and reaches a stable viscosity.

DETAILED DESCRIPTION OF THE EMBODIMENTS

All publications, patent applications, and issued patents mentioned herein are hereby incorporated in their entirety by reference. The citation of documents herein does not constitute an admission that those documents are prior art or have any relevance to the patentability of the invention disclosed herein. Any discussion of the content of documents cited in the Introduction is intended merely to provide a general summary of assertions made by the authors of the documents, and does not constitute an admission as to the accuracy of the content of such documents.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this invention and, unless explicitly stated otherwise, are not intended to be a representation that given embodiments of this invention have, or have not, been made or tested.

All percentages used herein are by weight of the total dentifrice composition, unless otherwise specified. The ratios used herein are weight ratios of the respective components, unless otherwise specified. All measurements are made at 25° C., unless otherwise specified.

As used throughout, ranges are used as a shorthand for describing each and every value that is within the range. Any value within the range can be selected as the terminus of the range.

Herein, "effective amount" means an amount of a compound or composition sufficient to significantly induce a positive benefit, preferably an oral health benefit, but low enough to avoid serious side effects, i.e., to provide a reasonable benefit to risk ratio, within the sound judgment of a skilled artisan.

A dentifrice composition is a product, which in the ordinary course of administration, is not intentionally swallowed for purposes of systemic administration of particular therapeutic agents, but is rather retained in the oral cavity for a time sufficient to contact substantially all of the tooth surfaces and/or oral tissues for purposes of oral activity. A dentifrice composition of the present invention may be in the form of a toothpaste or dentifrice. The term "dentifrice," as used herein, means paste or gel formulations unless otherwise specified. The dentifrice composition may be in any desired form, such as deep striped, surface striped, multi-layered, having the gel surrounding the paste, or any combination thereof.

The phrase "aqueous carrier" as used herein means any safe and effective materials for use in the compositions of the present embodiments. Such materials include thickening agents, humectants, ionic active ingredients, buffering agents, anticalculus agents, abrasive polishing materials, oxidizing agents, whitening agents, peroxide sources, alkali metal bicarbonate salts, surfactants, titanium dioxide, coloring agents, flavor systems, sweetening agents, antimicrobial agents, herbal agents, desensitizing agents, stain reducing agents, and mixtures thereof.

The embodiments described herein relate to a dentifrice composition having a phase with a low water content (e.g., zero water added) and containing an orally acceptable vehicle, a source of fluoride ions, a source of stannous ions, a source of zinc ions, at least one polyphosphate salt, and at least one acid, in a base comprising calcium pyrophosphate. The polyphosphate salt may be inorganic polyphosphate salts which have three or less phosphorous atoms, such as pyrophosphates and tripolyphosphates.

The inventors have unexpectedly discovered that compared to a traditional low-water silica-based dentifrice composition, a low-water composition based on calcium pyrophosphate abrasive provides better long term stability and oral bioavailability for stannous and fluoride in the composition. In particular, it was unexpectedly found that stannous fluoride was compatible with the calcium pyrophosphate in these low-water compositions, despite the traditional belief that stannous fluoride is incompatible with calcium based systems.

In one embodiment, the present disclosure provides a dentifrice composition (Composition 1) comprising: an orally acceptable vehicle; calcium pyrophosphate; a source of stannous ions (e.g., at least one); a source of zinc ions (e.g., at least one); a source of fluoride ions (e.g., at least one); an acid (e.g., at least one); and a polyphosphate salt (e.g., at least one) selected from the group consisting of inorganic polyphosphate salts which have equal to or less than three phosphorous atoms; wherein the dentifrice composition is a low-water composition (e.g., 1% water or less).

In further embodiments, the present disclosure provides the following compositions:

1.1 Composition 1, wherein the pH is from 3 to 8, e.g., from 4 to 7, or, e.g., from 5 to 6, or e.g., about 5.5, 5.75 or 5.8.

1.2 Composition 1 or 1.1, wherein the acid is selected from the group consisting of an inorganic acid (e.g., phosphoric acid, sulfuric acid, or hydrochloric acid) or an organic acid (e.g., acetic acid, citric acid, lactic acid, tartaric acid, gluconic acid, ascorbic acid, fumaric acid, formic acid, pyruvic acid, maleic acid, caprylic acid, capric acid, or caproic acid) or an amino acid (e.g., aspartic acid or glutamic acid).

1.3 Composition 1.2, wherein the acid is phosphoric acid.

1.4 Composition 1 or 1.1-1.3, wherein the polyphosphate is selected from the group consisting of an alkali metal salt of a pyrophosphate, an alkali metal salt of a tripolyphosphate, and mixtures thereof.

1.5 Composition 1.4, wherein the polyphosphate is selected from the group consisting of tetrasodium pyrophosphate, sodium tripolyphosphate, sodium acid pyrophosphate, and mixtures thereof.

1.6 Composition 1.5, wherein the polyphosphate comprises a mixture of tetrasodium pyrophosphate and sodium tripolyphosphate, optionally in a ratio of 1:1, 1:1.5, 1:2, 1:3, 1:5, 1:7, 1:9 or 1:11.

1.7 Composition 1 or 1.1-1.6, wherein the polyphosphate comprises from 1% to 10% by weight of the composition, e.g., from 3% to 7%, or, e.g., from 1% to 4%, or, e.g., from 4% to 8%.

1.8 Composition 1.7, wherein the polyphosphate comprises from 3% to 7% by weight of the composition.

1.9 Composition 1 or 1.1-1.8, wherein the source of stannous ions is selected from the group consisting of stannous fluoride, stannous gluconate, stannous phosphate, stannous pyrophosphate, stannous acetate, stannous sulfate, or stannous chloride.

1.10 Composition 1 or 1.1-1.9, wherein the source of fluoride ions is selected from the group consisting of sodium fluoride, potassium fluoride, stannous fluoride, or sodium monofluorophosphate.

1.11 Composition 1.10, wherein the source of fluoride ions and the source of stannous ions comprises stannous fluoride.

1.12 Composition 1 or 1.1-1.11, wherein the source of zinc ions comprises a zinc salt of an organic acid, or a zinc salt of an inorganic acid, or a zinc base.

1.13 Composition 1.12, wherein the source of zinc ions comprises zinc oxide, zinc chloride, zinc citrate, zinc malate, zinc lactate, zinc gluconate, zinc fluoride, zinc phosphate, zinc acetate, zinc sulfate or zinc tartrate.

1.14 Composition 1 or 1.1-1.13, further comprising an aqueous buffer system for the source of stannous ions.

1.15 Composition 1.14, wherein the buffer system is adapted to chelate the stannous ions in the composition.

1.16 Composition 1.15, wherein the buffer system comprises at least one of an organic acid or an alkali metal salt thereof.

1.17 Composition 1.16, wherein the organic acid is citric acid.

1.18 Composition 1.17, wherein the buffer system comprises a mixture of citric acid and trisodium citrate.

1.19 Composition 1.18, wherein the buffer system comprises from 0.1 to 10 weight % of the composition, e.g., from 1% to 5%, or e.g., from 2% to 3%.

1.20 Composition 1 or 1.1-1.19, wherein the calcium pyrophosphate comprises from 1 to 50% by weight of the composition, e.g., 10 to 50%, or e.g., 10 to 40%, or e.g., 15 to 40%, or e.g., 15 to 30%, or e.g., 20 to 30%, or about 20%.

1.21 Composition 1 or 1.1-1.20, wherein the dentifrice composition comprises 0% water based on the weight of the composition.

1.22 Composition 1 or 1.1-1.21, further comprising at least one humectant selected from the group consisting of glycerin, polyethylene glycol, propylene glycol, sorbitol, xylitol, other edible polyhydric alcohols, and mixtures thereof.

1.23 Composition 1.22, wherein the at least one humectant comprises from 0.1% to 70% by weight of the composition, e.g., from 1% to 60%, or, e.g., from 15% to 55%.

1.24 Composition 1 or 1.1-1.23, further comprising a desensitizing agent (e.g., a potassium salt or a strontium salt), such as potassium nitrate.

1.25 Composition 1 or 1.1-1.24, further comprising a thickening agent.

1.26 Composition 1.25, wherein the thickening agent comprises from 0.05 to 3% by weight of the composition, e.g., from 0.1 to 1.5% by weight of the composition.

1.27 Composition 1 or 1.1-1.26, wherein the viscosity remains between 100,000 and 300,000 centipoise at 25° C. for at least 30 days after formulation.

1.28 Composition 1.27, wherein the viscosity remains between 100,000 and 200,000 centipoise at 25° C. for at least 30 days after formulation.

1.29 Composition 1 or 1.1-1.28, wherein the composition is a single phase.

1.30 Composition 1 or 1.1-1.29, wherein the composition has a pH of from 5 to 9, e.g., from 6 to 8, or, e.g., from 7 to 8, or e.g., about 7.5 or about 7.75, as an aqueous suspension (e.g., a 5-20% w/w aqueous suspension, or, e.g., a 10-20% w/w aqueous suspension, or about a 10% w/w aqueous suspension).

1.31 Composition 1 or 1.1-1.30, wherein the calcium pyrophosphate is selected from calcium pyrophosphate tetrahydrate, calcium pyrophosphate dihydrate or calcium pyrophosphate anhydrous (either the α-phase, β-phase or γ-phase, or combinations), or mixtures thereof.

1.32 Composition 1 or 1.1-1.31, further comprising a secondary polishing agent (e.g., a secondary abrasive).

1.33 Composition 1.32, wherein the secondary polishing agent is selected from the group consisting of calcium phosphate, silicas (including gels and precipitates, such as silica xerogels and precipitated silica materials); aluminas (e.g., hydrated alumina); phosphates including orthophosphates (e.g. dicalcium orthophosphate dihydrate, tricalcium phosphate), polymetaphosphates (e.g., calcium polymetaphosphate, sodium polymetaphosphate), and pyrophosphates (e.g., a salt form or polymorph of calcium pyrophosphate that is different from the primary calcium phosphate, e.g., beta-phase calcium phosphate).

1.34 Composition 1 or 1.1-1.33, wherein the composition contains a greater amount of calcium pyrophosphate than silica, on a weight percentage basis of the composition.

1.35 Composition 1 or 1.1-1.33, wherein the composition does not contain any abrasive silicas.

1.36 Composition 1 or 1.1-1.34, wherein calcium pyrophosphate is the only abrasive agent.

1.37 Composition 1 or 1.1-1.36, wherein the only silica present is fumed silica, hydrated silica, or a mixture thereof (e.g. 0-5% by weight).

1.38 Composition 1 or 1.1-1.37, further comprising an additional source of fluoride ions (e.g., sodium fluoride, potassium fluoride, or sodium monofluorophosphate).

The polyphosphate may be selected from the group consisting of an alkali metal salt (e.g., lithium, sodium or potassium) of a pyrophosphate or a tripolyphosphate, preferably the at least one polyphosphate is selected from the group consisting of tetrasodium pyrophosphate, sodium tripolyphosphate, sodium acid pyrophosphate, tetrapotassium pyrophosphate, potassium tripolyphosphate or potassium acid pyrophosphate. In some embodiments, the polyphosphate may comprise a mixture of tetraalkali pyrophosphate and alkali tripolyphosphate, for example, a mixture of tetrasodium pyrophosphate and sodium tripolyphosphate. The polyphosphate may comprise from 1 to 10 wt % of the composition, preferably from 3 to 7 wt % of the composition.

Preferably, the source of fluoride ions and the source of stannous ions comprise stannous fluoride. Preferably, the source of zinc ions comprises a zinc salt of an organic acid, preferably zinc citrate, zinc lactate, or zinc gluconate, and more preferably zinc citrate. The source of zinc ions may also comprise any zinc compound including, for example, zinc oxide, zinc tartrate, zinc gluconate, and the like. Optionally, the composition any comprise a second source of fluoride, preferably sodium fluoride or sodium monofluorophosphate.

The inventors have unexpectedly found that a low-water dentifrice composition, based on calcium pyrophosphate, and comprising a stannous source, a zinc source and a fluoride source, is protected against loss of bioavailable stannous and/or zinc during storage by the inclusion of an effective amount of acid to lower the pH to the desirable range. The pH range of the dentifrice composition is preferably from pH 2 to pH 7, more preferably pH 3 to pH 6, e.g., pH 4 to pH 6, or, e.g., pH 5 to pH 6, for example, about pH 5.5, 5.75 or 5.8. Preferably the acid is a strong inorganic acid (e.g., phosphoric acid, sulfuric acid, hydrochloric acid). Upon dilution into water (e.g., a 10% aqueous solution or suspension), as would occur upon consumer usage of the dentifrice composition, the solubilization of the components results in a higher pH. For example, a 10% w/w aqueous suspension of the dentifrice composition is preferably from pH 5 to 9, e.g., from 6 to 8, or, e.g., from 7 to 8, or e.g., about 7.5 or about 7.75.

The vehicle may include a thickening agent comprising at least one of a cross-linked polyvinylpyrrolidone. The cross-linked polyvinylpyrrolidone may comprise a homopolymer of N-vinyl-2-pyrrolidone. The cross-linked polyvinylpyrrolidone may comprise from 0.05 to 15 wt % of the composition, preferably from 0.75 to 1.25 wt % of the composition.

In the dentifrice composition, the thickening agent may further comprise at least one of a cellulose and a synthetic block copolymer of ethylene oxide and propylene oxide.

In the dentifrice composition, the composition may further comprise at least one humectant selected from the group consisting of glycerin, polyethylene glycol, propylene glycol, and mixtures thereof.

Optionally, the composition further comprises an aqueous buffer system for the source of stannous ions. The buffer system may be adapted to chelate the stannous ions in the composition. The buffer system may comprise at least one of a weak organic acid or an alkali metal salt thereof, the organic acid preferably being citric acid. The buffer system may comprise a mixture of citric acid and trisodium citrate. The buffer system may comprise from 0.1% to 10% by weight of the composition, e.g., 1 to 5 weight % of the composition. The buffer system may be present, by weight, in an amount that is greater than the amount, by weight, of the source of stannous ions. "Aqueous buffer system", as used herein, refers to the acidic and/or basic components of a buffer system that would result in an aqueous buffer system when the composition is dissolved or suspended in water.

The use of the buffer system described herein is believed to reduce or eliminate precipitation of insoluble stannous compounds. While not intending to be bound by any theory of operation, the inventors believe that an aqueous buffer system, e.g. a citrate buffer system, which may be employed as a premix for the stannous salt to chelate the stannous ions, can reduce or eliminate the precipitation of insoluble stannous compounds in the presence of zinc ions and polyphosphates in a low water dentifrice composition.

The preferred embodiments can provide a dentifrice that provides multiple therapeutic benefits by combining stannous ions and fluoride ions, e.g. as stannous fluoride, zinc ions, e.g. as zinc citrate, and polyphosphates, e.g. in the form of tetrasodium pyrophosphate/sodium tripolyphosphate. The use of a particular acid and/or pH, or a particular buffer system, can stabilize the stannous ions in the presence of the zinc ions and polyphosphates, and leave the stannous ions active in the single phase low water composition for effective anti-microbial action when used for cleaning the teeth.

While the specification concludes with claims particularly pointing out and distinctly claiming the invention, it is believed that the present invention will be better understood from the following description of preferred embodiments.

Polyphosphate Source

The present embodiments include a polyphosphate source. Polyphosphates are known to help retard calculus formation. However, it is also known that polyphosphates with an average chain length greater than 4 will also react with ionic fluoride in oral compositions at ambient temperature and produce monofluorophosphate ions, in addition to altering the pH of the composition. This reaction may compromise the efficacy of the oral composition and its ability to provide stable ionic fluoride and polyphosphate to the oral surfaces. It also is known that to have stable polyphosphate, the total water content and pH of the dentifrice composition should be controlled to reduce the hydrolysis of the polyphosphate.

A polyphosphate generally is understood to consist of two or more phosphate functional groups arranged primarily in a linear configuration, although some cyclic derivatives may be present. The preferred inorganic polyphosphate salts, which are preferably alkali metal salts, used in the dentifrice compositions of the present invention have no more than three phosphorous atoms, such as a pyrophosphate, for example tetrasodium pyrophosphate, or a polyphosphate, for example sodium tripolyphosphate. These polyphosphates may be used alone or in any combination thereof.

An effective amount of a polyphosphate source may be from 0.1% to 30%, preferably from 1% to 26%, more preferably from 4% to 20%, and most preferably from 5% to 13%, by weight of the total dentifrice composition. A typical range is from 1% to 10% by weight of the total dentifrice composition, more typically from 3% to 7% by weight of the total dentifrice composition. Preferably, the composition comprises tetrasodium pyrophosphate and sodium tripolyphosphate, in a ratio of from 1:1 to 1:12, for example, 1:1, 1:1.5, 1:2, 1:3, 1:5, 1:7, 1:9 or 1:11.

Aqueous Carriers

In preparing the present compositions, it is desirable to add one or more aqueous carriers to the compositions. Such materials are well known in the art and are readily chosen by one skilled in the art based on the physical and aesthetic properties desired for the compositions being prepared. Aqueous carriers typically comprise from 30% to 90%, preferably from 50% to 85%, and more preferably from 50% to 70%, by weight of the dentifrice composition.

Total Water Content

The compositions of the present disclosure are low-water compositions, meaning that they comprise 1% or less of added water, for example, no water added".

As used herein, any particular weight percentage of water in the composition refers to "added water", and this includes water that is added directly to the composition during manufacture, as well as water that is added as part of other ingredients during manufacture. For example, the addition of an 85% phosphoric acid ingredient to the composition necessarily means that 15% of the weight added is water. Common ingredients that may be added to oral care compositions as aqueous mixtures include polyols (such as glycerol and sorbitol), acids (e.g., 35 wt % hydrochloric acid, 85 wt % phosphoric acid, 98 wt % sulfuric acid), and polymers (such as carboxymethylcellulose or methyl vinyl ether/maleic anhydride copolymers), as well as any ingredients typically sold as solutions in water (for example, surfactants, coloring agents, flavoring agents, and the like). Added water also includes the water of hydration of inorganic salts, for example, the water contained in sodium citrate dihydrate, or zinc lactate dihydrate. Standard methods of water content analysis, such as the Karl Fischer method, typically are capable of measuring the water content of a composition derived from this "added water". A low water composition, as used herein, refers to a composition containing up to 1% by weight of "added water", which may or may not include actual water added to the composition. For example, if a single ingredient of the composition was present at 10% by weight of the composition, and that ingredient contained 10% by weight of water (e.g., a 90% glycerin solution) and this was the only water added, then the resulting composition would contain 1% by weight of water.

Water content, total water, or added water, as used herein, does not include the water that may be reversibly or irreversibly carried by hygroscopic ingredients such as silica. Such compounds are also known as desiccants or deliquescents. Such compounds are capable of trapping (adsorbing or absorbing) from the atmosphere moisture in a way that is typically very difficult to remove (for example, requiring application of high heat and vacuum). Such water may be practically irreversibly bound to the ingredient. Such quantities of water are not typically capable of measurement using common moisture analysis methods, such as the Karl Fischer method. Other strongly hygroscopic compounds include calcium chloride, magnesium chloride, calcium sulfate, magnesium sulfate, potassium phosphate, and the like. Thus, "0% water" or "zero water" compositions, as used herein, refer to "no water added" compositions, which may contain from 0% to 5% by weight of water trapped in hygroscopic, desiccant or deliquescent ingredients such as silica. Typically, however, such a composition will usually appear to be water-free or substantially water-free as measured using common water content analysis techniques, such as the Karl Fischer method.

In such low levels of water, polyphosphates and actives such as fluoride and stannous are not dissolved in the compositions herein. However, these ingredients may be dissolved in the present compositions in other low polar solvents. This allows the actives to remain stable in the compositions during storage. The fluoride ion and the stannous ion if present will be released from their salt forms or non-ionic solution forms when contacted with saliva and/or water at the time of brushing. Thus there is no need to physically separate the polyphosphate-containing portion of the composition from the ionic active-containing portion of the composition, for example by using a dual compartmented package. In addition, fluoride ion from a variety of sources may be used efficaciously in the present composition; there is no preference for the use of sodium monofluorophosphate as the fluoride ion source that is most compatible with the polyphosphate in the composition as previously described in U.S. Pat. No. 6,190,644, "Dentifrice Compositions Containing Polyphosphate and Sodium Monofluorophosphate."

Binder System

In some embodiments, the dentifrice compositions of the present disclosure may incorporate a binder system incorporating a cross-linked polyvinylpyrrolidone in combination with a gum. The binder system may further incorporate at least one additional thickening agent selected from the group consisting of polysaccharides, carbomers, poloxamers, modified celluloses, and mixtures thereof, and at least one humectant. The thickening agent comprises from 0.05% to 3%, and preferably from 0.1% to 1.5%, by weight of the composition. These binder systems provide desirable consistency and gellation to the low water composition. It has previously been known that gelling materials that provide desirable rheology with water and humectant provide generally less satisfactory rheology when the water is not present to activate their gellation binding properties. This is believed to be especially true of glycerin humectant. The binder system may further comprise additional inorganic thickening agents.

Thickening Agent

Polysaccharides, including gums, which are suitable for use herein include carageenans, gellan gum, locust bean gum, xanthan gum, and mixtures thereof. Carageenan is a polysaccharide derived from seaweed and has been known for use as a binder or thickener in toothpastes, see, e.g., U.S. Pat. Nos. 6,187,293 B1 and 6,162,418. There are several types of carageenan that may be distinguished by their seaweed source and/or by their degree of and position of sulfation. Suitable for use in the present invention are kappa carageenans, modified kappa carageenans, iota carageenans, modified iota carageenans, and mixtures thereof. Carageenans suitable for use herein include those commercially available from the FMC Company under the series designation "Viscarin," including but not limited to Viscarin TP 329, Viscarin TP 388, and Viscarin TP 389.

Gellan gum is another polysaccharide that is suitable for use herein. It is a polysaccharide aerobically fermented by *pseudomonas elodea*. It can also form an acceptable low water matrix when it is present at a level of from 0.1% to 3%, preferably from 0.4% to 1.8%.

Locust bean gum and xanthan gum are also suitable polysaccharides for use herein. Locust bean gum or xanthan gum as thickening agents can form a stable and acceptable dentifrice matrix when water level is lower than 10% in the composition.

Poloxamers are also suitable as thickening agents in the low water matrix herein. Poloxamer is a synthetic block copolymer of ethylene oxide and propylene oxide. It is available in several types. Herein, poloxamer 407 is preferable. It can be partly dissolved in water. When the temperature is higher than 65° C., it can dissolve in glycerin. POLOXAMER 407 ® is available, for example, from the BASF CORPORATION, New Jersey, USA.

Carbomers are also suitable as thickening agents in a low water matrix, especially in a zero-water matrix.

Modified celluloses such as hydroxyethyl cellulose are also good thickening agents in low water matrix. Since the water level is limited in the present compositions, modified hydroxyethyl cellulose with a hydrophobic chain ($C_{12}$-$C_{20}$) are preferred to increase the solubility and hydration of this thickening agent in other low polar solvents, such as glycerin, propylene glycol and PEG.

The dentifrice composition may further comprise additional inorganic thickening agents such as colloidal magnesium aluminum silicate or finely divided silica to further improve texture. Silicas used for thickening can be distinguished from silicas used as abrasives based on their physical properties, and the distinction is known to those skilled in the art. Additional inorganic thickening agents if present can be used in an amount from 0.1% to 15%, more preferably from 0.1% to 5%, by weight of the dentifrice composition.

Humectant

The humectant serves to keep toothpaste compositions from hardening upon exposure to air and certain humectants can also impart desirable sweetness of flavor to toothpaste compositions. Suitable humectants for use in the invention include glycerin, sorbitol, polyethylene glycol, propylene glycol, xylitol, and other edible polyhydric alcohols. Preferred are glycerin, polyethylene glycol, polypropylene glycol, and mixtures thereof, especially mixtures thereof. The humectant generally comprises from 0.1% to 70%, preferably from 1% to 60%, and more preferably from 15% to 55%, by weight of the composition.

The humectant is believed to have a significant impact on the viscosity of the low water matrix. For example, when using polysaccharide as the thickening agent in the composition, the viscosity of the matrix will increase when the level of glycerin or polyethylene glycol increases. On the contrary, the viscosity of matrix will decrease when the level of propylene glycol increases in the composition.

Ionic Active Ingredient

The dentifrice compositions of the present disclosure comprise an effective amount of a fluoride ion source, a stannous ion source, and a zinc ion source.

Fluoride Ion Source

The fluoride ion source herein is a soluble fluoride source capable of providing free fluoride ions. Soluble fluoride ion sources include sodium fluoride, stannous fluoride, indium fluoride, zinc fluoride, and sodium monofluorophosphate. Sodium fluoride, sodium monofluorophosphate and stannous fluoride are the preferred soluble fluoride ion sources. Norris et al., U.S. Pat. No. 2,946,725, issued Jul. 26, 1960, and Widder et al., U.S. Pat. No. 3,678,154 issued Jul. 18, 1972, disclose such fluoride ion sources as well as others. Optionally, the composition may contain more than one fluoride ion source.

The fluoride ion source in the present compositions preferably is present as a solid dispersion in the composition during storage, prior to actual brushing usage of the composition by a consumer. The level of water in the present compositions is too low to permit the fluoride source to dissolve in the composition during storage. Thus, there is no obvious interaction between the fluoride ion and the polyphosphate, or silica if present, during storage, providing a stable composition during storage. When the composition is contacted by saliva and/or water at the time of brushing, the fluoride source preferably will be dispersed and the active ion will be delivered to the oral cavity.

The present compositions may contain a soluble fluoride ion source capable of providing from 50 ppm to 3500 ppm, and preferably from 500 ppm to 3000 ppm of free fluoride ions. To deliver the desired amount of fluoride ions, fluoride ion source may be present in the total dentifrice composition at an amount of from 0.1% to 5%, preferably from 0.2% to 1%, and more preferably from 0.3 to 0.6%, by weight of the total dentifrice composition.

Metal Ion Source

The present disclosure comprises a source of stannous ions and zinc ions. The metal ion source can be a soluble or a sparingly soluble compound of stannous or zinc with inorganic or organic counter ions. Examples include the fluoride, chloride, chlorofluoride, acetate, hexafluorozirconate, sulfate, tartrate, gluconate, citrate, malate, glycinate, pyrophosphate, metaphosphate, oxalate, phosphate, carbonate salts and oxides of stannous and zinc.

Stannous and zinc ions have been found to help in the reduction of gingivitis, plaque, sensitivity, and improved breath benefits. The efficacy of these metal ions in the present compositions is not reduced by the polyphosphate.

Stannous and zinc ions are derived from the metal ion source(s) found in the dentifrice composition in an effective amount. An effective amount is defined as from at least 1000 ppm metal ion, preferably 2,000 ppm to 15,000 ppm. More preferably, metal ions are present in an amount from 3,000 ppm to 13,000 ppm and even more preferably from 4,000 ppm to 10,000 ppm. This is the total amount of metal ions (stannous and zinc and mixtures thereof) that is present in the compositions for delivery to the tooth surface.

The metal ion sources in the present compositions are preferably not fully ionized in the composition during storage, prior to actual brushing usage of the composition by a consumer. The level of water in the present compositions is too low to permit the metal ion source to dissolve in the composition during storage. But certain salts such as stannous chloride and stannous fluoride, can be solubilized in glycerin or propylene glycol. Both humectants can provide super stability protection for such stannous salts and also can provide a better taste profile than a water (aqueous) solution of stannous. When the composition is contacted by saliva and/or water at the time of brushing, the stannous ion source will be fully ionized and the active ion will be delivered to the oral cavity.

Dentifrices containing stannous salts, particularly stannous fluoride and stannous chloride, are described in U.S. Pat. No. 5,004,597 to Majeti et al. Other descriptions of stannous salt dentifrices are found in U.S. Pat. No. 5,578,293. The preferred stannous salts are stannous fluoride and stannous chloride dihydrate. Other suitable stannous salts include stannous acetate, stannous tartrate, stannous pyrophosphate and sodium stannous citrate. Examples of suitable zinc ion sources are zinc oxide, zinc sulfate, zinc chloride, zinc citrate, zinc lactate, zinc gluconate, zinc malate, zinc tartrate, zinc carbonate, zinc phosphate, and other salts listed in U.S. Pat. No. 4,022,880.

The combined metal ion source(s) will be present in an amount of from 0.25% to 11%, by weight of the final composition. Preferably, the metal ion sources are present in an amount of from 0.4 to 7%, more preferably from 0.45% to 5%.

Acid

The compositions described here also contain an acid in order to result in a composition with desired pH. As used herein, acid refers to a Bronsted acid that is capable of donating protons and resulting in a solution or suspension with a lower pH than would be obtained in the absence of the acid. Suitable acids for this purpose include strong inorganic acids, such as phosphoric acid, sulfuric acid, and hydrochloric acid. The acid may also be a weak inorganic acid, such as acetic acid, citric acid, lactic acid, tartaric acid, gluconic acid, ascorbic acid, fumaric acid, formic acid, pyruvic acid, maleic acid, caprylic acid, capric acid, or caproic acid. The acid may also be an amino acid, such as aspartic acid or glutamic acid. This added acid is in addition to any transiently formed acidic compounds derived from the reversible protonation of a conjugate base present in the composition (e.g., transiently present citric acid resulting from the presence of a citrate salt in a composition).

The inventors have surprisingly discovered that at low pH, a low-water or zero-water dentifrice composition can be preserved against loss of bioavailable metal ion by adjusting the composition to an acidic pH. The desired pH of the composition of the present disclosure is from pH 3 to pH 8, preferably from pH 4 to pH 7, e.g., pH 5 to pH 6, or, e.g., about pH 5.5.

Buffering Agent

The compositions described herein also may contain one or more buffering agents. Buffering agents, as used herein, refer to agents that can be used to maintain the pH of the compositions in the desired range. Suitable buffering agents include, but are not limited to, alkali metal hydroxides, ammonium hydroxide, organic ammonium compounds, carbonates, sesquicarbonates, borates, silicates, phosphates, imidazole, and mixtures thereof. Specific buffering agents include monosodium phosphate, trisodium phosphate, sodium benzoate, benzoic acid, sodium hydroxide, potassium hydroxide, alkali metal carbonate salts, sodium carbonate, imidazole, pyrophosphate salts, citric acid, and sodium citrate. Buffering agents are used at a level of from 0.1% to 30%, preferably from 0.1% to 10%, and more preferably from 0.3% to 3%, by weight of the present composition.

Anticalculus Agents

The compositions described herein also may employ, as anticalculus agents, polyphosphate materials known to be effective in reducing calcium phosphate mineral deposition related to calculus formation. Agents included are pyrophosphates, and tripolyphosphates. The compositions may also employ synthetic anionic polymers [including polyacrylates and copolymers of maleic anhydride or acid and methyl vinyl ether (e.g., GANTREZ®), as described, for example, in U.S. Pat. No. 4,627,977 to Gaffar et al.; as well as, e.g., polyamino propane sulfonic acid (AMPS)], zinc citrate trihydrate, diphosphonates (e.g., EHDP; AHP), polypeptides (such as polyaspartic and polyglutamic acids), and mixtures thereof.

Abrasive Polishing Materials

One or more secondary abrasive polishing materials may also be included in the toothpaste compositions. The abrasive polishing material contemplated for use in the compositions of the present invention can be any material that does not excessively abrade dentin. Typical abrasive polishing materials include silicas including gels and precipitates; aluminas; phosphates including orthophosphates, polymetaphosphates, and pyrophosphates; and mixtures thereof. Specific examples include dicalcium orthophosphate dihydrate, tricalcium phosphate, calcium polymetaphosphate, insoluble sodium polymetaphosphate, hydrated alumina, beta calcium pyrophosphate, calcium carbonate, and resinous abrasive materials such as particulate condensation products of urea and formaldehyde, and others such as disclosed by Cooley et al in U.S. Pat. No. 3,070,510, issued Dec. 25, 1962. Mixtures of abrasives may also be, used. If the dentifrice composition or particular phase comprises a polyphosphate having an average chain length of 4 or more, calcium containing abrasives and alumina are not preferred abrasives. The most preferred secondary abrasive is silica.

Calcium pyrophosphate can exist in several forms, including as the anhydrous form, the dihydrate form and the tetrahydrate form. The anhydrous form of calcium phosphate can also exist in three distinct polymorphs, known as the alpha, beta and gamma forms (or phases). Calcium pyrophosphate anhydrous can be converted to one phase or another by the application of heat and/or cooling, although the gamma phase is considered only metastable. The primary base abrasive of the present disclosure, calcium pyrophosphate, can be present in any of these forms, or as a mixture thereof. Where the base calcium pyrophosphate is present as a specific form or salt, then an alternate form or salt of calcium pyrophosphate may be present as a secondary polishing agent. For example, the present disclosure can provide a composition containing 20% by weight of alpha-calcium pyrophosphate as the primary abrasive, with 2-5 wt % beta-calcium pyrophosphate as a secondary polishing agent.

Silica dental abrasives of various types are preferred as secondary polishing materials because of their unique benefits of exceptional dental cleaning and polishing performance without unduly abrading tooth enamel or dentine. The silica abrasive polishing materials herein, as well as other abrasives, generally have an average particle size ranging between 0.1 to 30 microns, and preferably from 5 to 15 microns. Silicas intended as abrasives can be distinguished from silicas used as thickeners or for other purposes based on such characteristics as particle size distribution, porosity, water content and method of preparation (e.g., precipitation versus colloidal). One skilled in the art is familiar with the distinction between abrasive and non-abrasive silicas. Abrasive silica can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975. Preferred are the silica xerogels marketed under the trade name "SYLOID®" by the W. R Grace & Company, Davison Chemical Division. Also preferred are the precipitated silica materials such as those marketed by the J. M. Huber Corporation under the trade name, "ZEODENT®", particularly the silica carrying the designation "Zeodent 119." The types of silica dental abrasives useful in the toothpastes of the present invention are described in more detail in Wason, U.S. Pat. No. 4,340,583, issued Jul. 29, 1982. Silica abrasives are also described in Rice, U.S. Pat. Nos. 5,589,160; 5,603,920; 5,651,958; 5,658,553; and 5,716,601. The secondary abrasive in the toothpaste compositions described herein is generally present at a level of from 1% to 5% by weight of the composition. Preferably, toothpastes contain from 1% to 3% of secondary abrasive, by weight of the dentifrice composition.

In some embodiments of the present disclosure, silica abrasives are present as secondary polishing agents. In other embodiments of the present disclosure, non-abrasive silicas may be present (e.g., hydrated silica and fumed silica). In some embodiments of the present disclosure, calcium pyrophosphate is the only abrasive present.

Peroxide Source

The present disclosure may include a peroxide source in the composition. The peroxide source may be selected from the group consisting of hydrogen peroxide, calcium peroxide, urea peroxide, and mixtures thereof. The preferred peroxide source is calcium peroxide. The following amounts represent the amount of peroxide raw material, although the peroxide source may contain ingredients other than the peroxide raw material. The present composition may contain from 0.01% to 10%, preferably from 0.1% to 5%, more preferably from 0.2% to 3%, and most preferably from 0.3% to 0.8% of a peroxide source, by weight of the dentifrice composition.

Additional Aqueous Carriers

The compositions also may comprise surfactants, also commonly referred to as sudsing agents. Suitable surfactants are those that are reasonably stable and foam throughout a wide pH range. The surfactant may be anionic, nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976.

Nonionic surfactants that can be used in the compositions can broadly be defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name PLURONIC®), polyoxyethylene, polyoxyethylene sorbitan esters (sold under trade name TWEENS®), Polyoxyl 40 hydrogenated castor oil, fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials. The amphoteric surfactants useful in the present invention can be broadly described as derivatives of aliphatic secondary and tertiary amines in which the aliphatic radical can be a straight chain or branched and wherein one of the aliphatic substituents contains from 8 to 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Many of these suitable nonionic and amphoteric surfactants are disclosed by Gieske et al. in U.S. Pat. No. 4,051,234. The present composition typically comprises one or more surfactants each at a level of from 0.25% to 12%, preferably from 0.5% to 8%, and most preferably from 1% to 6%, by weight of the composition.

Titanium dioxide may also be added to the present composition. Titanium dioxide is a white powder which adds opacity to the compositions. Titanium dioxide generally comprises from 0.25% to 5%, by weight of the composition.

Coloring agents may also be added to the present composition. The coloring agent may be in the form of an aqueous solution, preferably 1% coloring agent in a solution of water. Color solutions generally comprise from 0.01% to 5%, by weight of the composition.

A flavor system can also be added to the compositions. Suitable flavoring components include oil of wintergreen, oil of peppermint, oil of spearmint, clove bud oil, menthol, anethole, methyl salicylate, eucalyptol, *cassia,* 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. Coolants may also be part of the flavor system. Preferred coolants in the present compositions are the paramenthan carboxyamide agents such as N-ethyl-p-menthan-3-carboxamide (known commercially as "WS-3") and mixtures thereof. A flavor system is generally used in the compositions at levels of from 0.001% to 5%, by weight of the composition.

Sweetening agents can be added to the compositions. These include saccharin, dextrose, sucrose, lactose, xylitol, maltose, levulose, aspartame, sodium cyclamate, D-tryptophan, dihydrochalcones, acesulfame, and mixtures thereof. Sweetening agents are generally used in toothpastes at levels of from 0.005% to 5%, by weight of the composition.

The compositions of the present disclosure may also include other agents, such as antimicrobial agents. Included among such agents are water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides, polyphenols, and herbals. The water soluble antimicrobials include quaternary ammonium salts and bis-biquanide salts, among others. Triclosan monophosphate is a preferred additional water soluble antimicrobial agent. The quaternary ammonium agents include those in which one or two of the substitutes on the quaternary nitrogen has a carbon chain length (typically alkyl group) from 8 to 20, typically from 10 to 18 carbon atoms while the remaining substitutes (typically alkyl or benzyl group) have a lower number of carbon atoms, such as from 1 to 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethylstearyl ammonium chloride, cetyl pyridinium chloride, quaternized 5-amino-1,3-bis(2-ethyl-hexyl)-5-methyl hexa hydropyrimidine, benzalkonium chloride, benzethonium chloride and methyl benzethonium chloride are examplary of typical quaternary ammonium antibacterial agents. Other compounds are bis[4-(R-amino)-1-pyridinium] alkanes as disclosed in U.S. Pat. No. 4,206,215, issued Jun. 3, 1980, to Bailey.

An effective amount of a desensitizing agent may also be incorporated into the present compositions. The desensitizing agents include those selected from alkali, or alkaline earth metal, or aluminum salts with a chloride, nitrate, sulfate, or acetate anion. Preferred salts include potassium nitrate, potassium citrate, potassium chloride, strontium chloride, and mixtures thereof. Such desensitizing agents are disclosed in e.g., U.S. Pat. No. 5,718,885. Other desensitizing agents may be present that operate by occluding the dentinal tubules. Such agents include very fine small-particle inorganic materials, including silica, calcium carbonate, and arginine carbonate.

For compositions that contain stannous, a stain reducing agent such as Plasdone S-630 or aluminum hydrate may further be added to the composition. Plasdone is polyvinyl pyrrolidone (PVP) that can be synthesized by polymerizing vinylpyrrolidone. Commercially, it has been produced as a series of products having mean molecular weights ranging from 10,000 to 700,000. Herein, the low molecular weights and middle molecular weights (from 10,000 to 100,000) are preferred. In order to remove stain effectively, the level of PVP is preferably from 0.5% to 10%, more preferably from 1.0% to 7.0%, and even more preferably from 1.5% to 5.0%.

The dentifrice compositions may be a paste, gel, or any configuration or combination thereof. A further embodiment of the present invention includes dual-phase or multi-phase compositions comprising the present low-water compositions as one phase and at least one other separate phase comprising additional dentifrice components to further enhance stability, performance and/or aesthetics of the dentifrice product. For example, a dual phase composition may comprise a first phase comprising the present low-water composition with polyphosphate and ionic active(s) and a separate second phase comprising additional active agents such as bleaching agents, preferably a peroxide source, or a tooth surface conditioning agent to provide improved cleaning, whitening, anti-staining and mouth feel benefits. Examples of tooth conditioning agents are polysiloxanes and modified polysiloxanes, including diorganopolysiloxanes such as polydimethylsiloxane (PDMS); alkyl- and alkoxy-dimethicone copolyols such as $C_{12}$ to $C_{20}$ alkyl dimethicone copolyols; and aminoalkylsilicones. These siloxane polymers are described for example in U.S. Pat. Nos. 5,759,523; 6,024,891; 6,123,950; 6,019,962; 6,139,823.

The dispenser for the dentifrice compositions may be a tube, pump, or any other container suitable for dispensing toothpaste. In a dual phase oral composition, each oral composition will be contained in a physically separated compartment of a dispenser and dispensed side-by-side.

Methods of Use

In practicing the embodiments, the user need only apply the dentifrice composition herein, or an aqueous suspension thereof, to the tooth surfaces of a human or animal, in the areas desired, in order to obtain a desired effect, e.g., whitening, breath freshening, caries prevention, pain relief, gum health, tartar control, erosion control, etc. Use of dentifrices to control erosion of the tooth surface, or to prevent demineralization, are known and described in, for example, U.S. Pat. No. 6,685,920, the disclosure of which is incorporated by reference herein in its entirety. The compositions also may be applied to other oral cavity surfaces, such as the gingival or mucosal tissues, although it is believed that the benefits are best achieved when the dentifrice compositions are applied to the teeth. The dentifrice composition may contact the tooth and/or oral cavity surface either directly, or indirectly, however, it is preferred that the dentifrice composition be directly applied. The dentifrice composition may be applied by any means, but is preferably applied with a brush or by rinsing with a dentifrice slurry.

The manufacture of the oral composition of the present invention may be accomplished by any of the various standard techniques for producing such compositions. To make a dentifrice, a vehicle may be prepared containing humectant, for example, one or more of glycerin, glycerol, sorbitol, and propylene glycol, thickener agents and antibacterial agent such as triclosan, and the vehicle and a mixture of anionic and amphoteric surfactants are added, followed by blending in of a polishing agent, as well as fluoride salts, with the pre-mix.

The following examples are further illustrative of the preferred embodiments, but it is understood that the invention is not limited thereto.

Example 1

Dentifrice compositions are prepared having the formulations as indicated in Table 1. All compositions contain 0.45% by weight of stannous fluoride and 1% by weight of zinc oxide. Composition A is a 0% water calcium pyrophosphate composition with 0.5% phosphoric acid. Composition B is a 0% water calcium pyrophosphate composition with 0.25% phosphoric acid. Composition C is a 0% water abrasive silica composition. Composition D is a 10% water abrasive silica composition. Composition E is a high water abrasive silica composition. Compositions A and B contain calcium pyrophosphate as the only abrasive, and contain non-abrasive silica (hydrated or fumed silica).

TABLE 1

| Description | A | B | C | D | E |
| --- | --- | --- | --- | --- | --- |
| Demineralized Water | 0.00 | 0.00 | 0.00 | 10.000 | 15.28 |
| Sorbitol, 70% Aq Soln | | | | | 54.77 |
| Calcium Pyrophosphate Abrasive | 20.00 | 20.00 | | | |
| Stannous Fluoride | 0.45 | 0.45 | 0.45 | 0.45 | 0.45 |
| Zinc Oxide | 1.00 | 1.00 | 1.00 | 1.00 | 1.00 |
| Tetrasodium Pyrophosphate | 1.00 | 1.00 | 2.00 | 2.00 | 0.50 |
| Sodium Tripolyphosphate | 3.00 | 3.00 | 3.00 | 3.00 | |
| Sodium Acid Pyrophosphate | 2.00 | 1.00 | | | |
| Trisodium Citrate Dihydrate | | | | 3.00 | |
| Citric Acid Anhydrous | | | | 2.00 | |
| 99.0%-101.0% Glycerol | 30.46 | 31.76 | 41.95 | 40.64 | |
| Propylene Glycol | 15.95 | 15.95 | 10.80 | 4.00 | |
| Polyethylene Glycol | 6.31 | 6.31 | 7.00 | 3.00 | 3.00 |
| Polyvinyl pyrrolidone | 5.75 | 5.75 | 4.25 | 1.00 | |
| Silica-Abrasive | | | 12.00 | 12.00 | 10.00 |
| Silica-High Cleaning | | | 12.00 | 12.00 | |
| Fumed Silica | 1.75 | 1.75 | | | 5.00 |
| Silica-Thickener | | | | | 3.50 |
| Phosphoric Acid, 85% | 0.50 | 0.20 | | | |
| Sodium Saccharin | 0.30 | 0.30 | 0.80 | 0.60 | 0.30 |
| Carboxymethyl Cellulose | | | | 0.70 | 1.00 |
| Titanium Dioxide | | | 1.00 | 0.15 | 0.75 |
| Pluracare L1220 | 7.50 | 7.50 | | | |
| Sodium Lauryl Sulfate | 2.00 | 2.00 | 1.75 | 1.75 | 2.00 |
| Xanthan Gum | | | | 0.30 | |
| COCAMIDOPROPYL BETAINE | | | | 1.00 | 1.25 |
| Butylated Hydroxy Toluene | 0.03 | 0.03 | | | |
| Flavor | 2.00 | 2.00 | 2.00 | 1.40 | 1.20 |
| Total Components | 100.00 | 100.00 | 100.00 | 100.00 | 100.00 |
| pH | 5.8 | 5.8 | 6.6 | 5.3 | 6.8 |
| 10% pH | 7.4 | 8.9 | 9.1 | 6.8 | 7.7 |

The pH of the native composition is measured using a standard glass electrode pH meter by inserting the electrode into the composition. "10% pH" refers to the measurement of the pH of an aqueous suspension of the composition that is 10% w/w composition and 90% w/w deionized water. pH of the native composition is measured for purposes of comparison between different compositions and, owing to the low water content of the composition, may not reflect a true hydrogen ion concentration.

Example 2

The dentifrice compositions in accordance with Formula A through E are subjected to an accelerated aging study to determine the stability of the stannous ion, zinc ion and fluoride ion. The dentifrice compositions are subjected to a temperature of 40° C. for a period of 8 weeks or 13 weeks. The final amounts of soluble stannous, soluble zinc, and ionic fluoride, representing the available stannous ion, zinc ion and fluoride ion, respectively, are measured at the end of the test period. The results are shown in Table 2.

TABLE 2

|  | Formula | | | | |
| --- | --- | --- | --- | --- | --- |
|  | A | B | C | D | E |
| Formulated stannous (wt %) | 0.36 | 0.33 | 0.35 | 0.34 | 0.33 |
| 8-wk soluble stannous (wt %) | 0.29 | 0.29 | 0.14 | 0.29 | ND |
| 13-wk soluble stannous (wt %) | 0.26 | 0.25 | 0.12 | 0.34 | ND |
| Formulated zinc (wt %) | 0.88 | 0.87 | 0.76 | 0.72 | 0.72 |
| 8-wk soluble zinc (wt %) | 0.73 | 0.45 | 0.32 | 0.62 | 0.02 |
| 13-wk soluble zinc (wt %) | 0.34 | 0.44 | 0.34 | 0.60 | 0.04 |
| Initial ionic fluoride (ppm) | 1089 | 1062 | 1027 | 1020 | 1097 |
| 8-wk ionic fluoride (ppm) | 1051 | 1075 | 755 | 651 | 1078 |

Table 2 shows that the composition of Formulas A and B, containing calcium pyrophosphate instead of silica, have much improved availability of stannous, zinc and fluoride, compared to the silica-based formula C, D and E. the directly comparable low-water silica formula C shows much lower stannous and zinc at 8 and 12 weeks than Formulas A and B. The 10% water D formula shows acceptable zinc and stannous retention, but at the expense of considerable loss in fluoride. The traditional high water high-water composition E shows very poor metal ion availability, including no detectable soluble stannous at 8 or 13 weeks. Comparison of Formulas A and B shows that the higher pH formula A, containing twice the amount of phosphoric acid, results in a significant improvement in zinc ion stabilization.

What is claimed is:

1. A dentifrice composition comprising:
   an orally acceptable vehicle;
   calcium pyrophosphate, wherein the calcium pyrophosphate comprises from 10 to 40% by weight of the composition;
   a source of stannous ions;
   a source of zinc ions, wherein the source of zinc ions comprises zinc oxide;
   a source of fluoride ions;
   an acid, wherein the acid is phosphoric acid; and
   a polyphosphate salt selected from the group consisting of inorganic polyphosphate salts which have equal to or less than three phosphorous atoms;
   wherein the dentifrice composition has a total water content of less than about 1% based on the weight of the composition.

2. The composition of claim 1, wherein the composition has a pH of from 5 to 9, from 6 to 8, from 7 to 8, or about 7.5 or about 7.75, as an aqueous suspension.

3. The composition of claim 1, wherein the polyphosphate is selected from the group consisting of an alkali metal salt of a pyrophosphate, an alkali metal salt of a tripolyphosphate, and mixtures thereof.

4. The composition of claim 3, wherein the polyphosphate is selected from the group consisting of tetrasodium pyrophosphate, sodium tripolyphosphate, sodium acid pyrophosphate and mixtures thereof.

5. The composition of claim 4, wherein the polyphosphate comprises a mixture of tetrasodium pyrophosphate and sodium tripolyphosphate.

6. The composition of claim 1, wherein the polyphosphate comprises from 1 to 10% by weight of the composition.

7. The composition of claim 1, wherein the source of fluoride ions and the source of stannous ions comprises stannous fluoride.

8. The composition of claim 1, wherein the calcium pyrophosphate is selected from the group consisting of calcium pyrophosphate dihydrate, calcium pyrophosphate tetrahydrate, α-phase anhydrous calcium pyrophosphate, β-phase anhydrous calcium pyrophosphate, or a mixture thereof.

9. The composition of claim 1, wherein the calcium pyrophosphate comprises about 20% by weight of the composition.

10. The composition of claim 1, further comprising a secondary polishing agent.

11. The composition of claim 1, wherein the composition does not contain silica abrasive.

12. The composition of claim 1, wherein the dentifrice composition comprises 0% water based on the weight of the composition.

13. The composition of claim 1, further comprising at least one humectant selected from the group consisting of glycerin, polyethylene glycol, propylene glycol, and mixtures thereof.

14. The composition of claim 1, wherein the composition is a single phase.

15. The composition of claim 1, wherein the only abrasive present is calcium pyrophosphate.

* * * * *